US00RE40359E

(19) United States
(12) Reissued Patent
Katsarava et al.

(10) Patent Number: US RE40,359 E
(45) Date of Reissued Patent: Jun. 3, 2008

(54) POLYMER BLENDS AS BIODEGRADABLE MATRICES FOR PREPARING BIOCOMPOSITES

(75) Inventors: Ramaz Katsarava, Tbilisi (GE); Zemphira Alavidze, Tbilisi (GE)

(73) Assignee: SurModics, Inc., Eden Prairie, MN (US)

(21) Appl. No.: 11/372,447

(22) Filed: Mar. 8, 2006

Related U.S. Patent Documents

Reissue of:
(64) Patent No.: 6,703,040
Issued: Mar. 9, 2004
Appl. No.: 09/757,704
Filed: Jan. 11, 2001

U.S. Applications:
(60) Provisional application No. 60/175,377, filed on Jan. 11, 2000, provisional application No. 60/175,416, filed on Jan. 11, 2000, provisional application No. 60/205,240, filed on May 19, 2000, and provisional application No. 60/175,415, filed on Jan. 11, 2000.

(51) Int. Cl.
*C01B 31/26* (2006.01)

(52) U.S. Cl. ..... 424/444; 424/443; 424/445; 424/446; 424/447; 424/449

(58) Field of Classification Search ..... None
See application file for complete search history.

(56) References Cited

U.S. PATENT DOCUMENTS

| | | | | | |
|---|---|---|---|---|---|
| 3,493,652 | A | * | 2/1970 | Hartman | 424/94.6 |
| 3,867,520 | A | * | 2/1975 | Mori et al. | 424/449 |
| 4,351,337 | A | * | 9/1982 | Sidman | 424/425 |
| 4,414,202 | A | * | 11/1983 | Silvetti | 424/648 |
| 4,778,679 | A | * | 10/1988 | Silvetti | 424/648 |

(Continued)

FOREIGN PATENT DOCUMENTS

| | | | | |
|---|---|---|---|---|
| EP | 047719 | | * | 9/1991 |
| EP | 447719 | A1 | * | 9/1991 |
| EP | 0560014 | | * | 9/1993 |
| EP | 560014 | A1 | * | 9/1993 |
| EP | 0712635 | | * | 5/1996 |
| EP | 712635 | A1 | * | 5/1996 |
| JP | 04103566 | A | * | 4/1992 |
| JP | 04 103566 | A | | 6/1992 |
| WO | WO 9832398 | A1 | * | 7/1998 |
| WO | 9832398 | | * | 7/1998 |
| WO | WO 9832777 | A1 | * | 7/1998 |
| WO | 9832777 | | * | 7/1998 |
| WO | WO 03/062298 | A1 | | 7/2003 |

OTHER PUBLICATIONS

Saotome et al., "Novel Enzymatically Degradable Polymers Comprising a–Amino Acid, 1,2–Ethanediol, and Adipic acid", The Chemical Society of Japan, 1991, pp. 21–24.*
Grigorieva, et al., "Advances in Plastics Technology," Biodegradable Polymers for Medical Applications, 1999, (13 pgs).
Arabuli, et al, "Heterochain Polymers Based on Natural Amino Acids. Synthesis and Enzymatic Hydrolysis of Regular Polyester Amides Based on Bis(L–phenylalanine) α,ω–Alkylene Diesters and Adipic Acid," Macromolecular Chemistry and Physics, vol. 195, Jun. 1994, pp. 2279–2289.

(Continued)

*Primary Examiner*—Isis Ghali
(74) *Attorney, Agent, or Firm*—Kagan Binder, PLLC

(57) ABSTRACT

The present invention provides bioerodable constructs for controlled release of bioactive materials. In a preferred mode, the constructs may be utilized adjacent to a biological surface. The constructs are based on a blend of two or more poly(ester-amide) polymers (PEA). Such polymers may be prepared by polymerization of a diol (D), a dicarboxylic acid (C) and an alpha-amino acid (A) through ester and amide links in the form $(DACA)_n$. An example of a $(DACA)_n$ polymer is shown below in formula II. Suitable amino acids include any natural or synthetic alpha-amino acid, preferably neutral amino acids.

65 Claims, 1 Drawing Sheet

U.S. PATENT DOCUMENTS

| | | | | |
|---|---|---|---|---|
| 4,835,248 | A | | 5/1989 | Bader et al. |
| 4,876,242 | A | * | 10/1989 | Applebaum et al. ..... 514/3 |
| 5,093,319 | A | * | 3/1992 | Higham et al. ..... 514/55 |
| 5,306,620 | A | * | 4/1994 | Ginsberg et al. ..... 435/7.21 |
| 5,380,656 | A | * | 1/1995 | Barrett et al. ..... 435/219 |
| 5,386,003 | A | | 1/1995 | Greene et al. |
| 5,399,665 | A | | 3/1995 | Barrera et al. |
| 5,468,480 | A | * | 11/1995 | Barrett et al. ..... 424/94.65 |
| 5,658,592 | A | * | 8/1997 | Tanihara et al. ..... 424/488 |
| 5,770,229 | A | * | 6/1998 | Tanihara et al. ..... 424/488 |
| 5,902,875 | A | | 5/1999 | Roby et al. |
| 5,914,387 | A | | 6/1999 | Roby et al. |
| 5,919,893 | A | | 7/1999 | Roby et al. |
| 6,503,538 | B1 | | 1/2003 | Chu et al. |

OTHER PUBLICATIONS

Kharadze, et al, "Synthesis and α–Chymotrypsinolysis of Regular Polyester Amides Based on Phenylalanine, Diols, and Terephthalic Acid," Polymer Science, Series A, vol. 41, No. 9, Sep. 1999, pp. 883–890.

Castaldo, et al, "Synthesis and Preliminary Characterisation of Polyesteramides Containing Enzmatically Degradable Amide Bonds," Polymer Bulletin, vol. 28, No. 3, May 1992, pp. 301–307.

Paredes, et al, "Studies on the Biodegradation and Biocompatibility of a New Poly(ester amide) Derived from L–Alanine," Journal of Applied Polymer Science, vol. 69, No. 8, Aug. 22, 1998, pp. 1537–1549.

Rodriguez–Galan, et al, "Comparative Studies on the Degradability of Polyester Amides Derived from L– and L,D–Alanine," Journal of Applied Polymer Science, vol. 74, No. 9, Nov. 28, 1999, pp. 2312–2320.

Fan, et al, "Synthesis and Specific Biodegradation of Novel Polyesteramides Containing Amino Acid Residues," Journal of Polymer Science, Polymer Chemistry Edition 39, No. 9, May 1, 2001, pp. 1318–1328.

Grigorieva, et al, "Biodegradable Polymers for Medical Applications," Advances in Plastics Technology, Conference Papers, 3rd, Katowice, Poland, Nov. 16–18, 1999, Institute of Plastics and Paint Industry (Abstract only).

Saotome, et al, "Enzymic Degrading Solubilization of a Polymer Comprising Glycine, Phenylalanine, 1,2–Ethanediol, and Adipic Acid," the Chemical Society of Japan, Chemistry Letters, (1), 1991, pp. 153–154.

Y Saomote et al. "Novel Enzmatically Degradable Polymers Comprising α–Amino Acid, 1,2–Ethanediol, and Adipic Acid", Chemistry Letters 1991, 21–24.*

Katsarava et al., "Wound Dressing (PagoDerm)", Patent Department, Republic of Georgia, Jul. 1997, pp. 1 and 2.*

Katsarava, R., et al., "Amino Acid–Based Bioanalogous Polymers, Synthesis, and Study of Regular Poly(ester amide)s Based on Bis(α–amino acid) α,ω–Alkylene Diesters, and Aliphatic Dicarboxylic Acids," *Journal of Polymer Science: Part A: Polymer Chemistry,*37:391–407 (1999).*

J. S. Soothill, et al., "The Efficacy of Phages i the Prevention of the Destruction of Pig Skin In Vitro by *Pseudomonas aeruginosa," Med. Sci. Res.,*16:1287–1288 (1988).*

Y. Kuroyanagi, et al., "A Silver–Sulfadiazine–Impregregnated Synthetic Wound Dressing Composed of Poly–L–Leucine Spongy Matrix: An Evaluation of Clinical Cases," *J. Appl. Biomater.,*3;153–161 (1992).*

Y. Kuroyanagi, et al., "Evaluation of a Synthetic Wound Dressing Capable of Releasing Silver Sulfadiazine," *J. Burn Care Rehabil.,*12:106–115 (1991).*

J. Schwartz, "Science Looks to Engineers for Solutions to Medicine's Most Perplexing Problems," *Cornell Engineering Magazine,*pp. 5–10 (1997).*

Tsitalanadze, et al., "Amino Acid Based Bioanalogous Polymers. Some Biological Studies of Regular Poly(Ester Amide)s and Bioactive Composites Based on Them," International Symposium on *Biodegradable Materials,*p. 122, Hamburg, Germany (1996).*

R. Katsarava, et al., "Amino Acid–Based Bioanalogous Polymers. Synthesis, and Study of Regular Poly(ester amide)s Based on Bis(α–amino acid) α,ω–Alkylene Diesters, and Aliphatic Dicarboxylic Acids," *Journal of Polymer Science. Part A: Polymer Chemistry,*97:391–407 (1999).*

* cited by examiner

POLYMER BLENDS AS BIODEGRADABLE MATRICES FOR PREPARING BIOCOMPOSITES

Matter enclosed in heavy brackets [ ] appears in the original patent but forms no part of this reissue specification; matter printed in italics indicates the additions made by reissue.

This application claims benefit of Provisional Application No. 60/175,377 filed on Jan. 11, 2000 *and Provisional No. 60/175,415, filed Jan. 11, 2000* and Provisional No. 60/175,416 filed Jan. 11, 2000 and Provisional No. 60/205,240 filed on May 19, 2000.

BACKGROUND OF THE INVENTION

1. Field of the Invention

This invention is directed to polymeric matrices designed for controlled release of biologically active substances, such as therapeutic bacteriophage which can kill bacteria capable of causing disease.

2. Review of Related Art

Bioactive composites based on biodegradable (or more precisely, bioerodible) polymers as matrices, impregnated by bactericidal substances are promising for the treatment of superficial infected wounds. On the one hand, bactericidal substances clean the wound from bacteria and make favorable conditions for wound healing, and prevent bacterial invasion through the holes made in wound coverings for exudate [drainage, on] *drainage. On* the other hand, biodegradable polymer which is able to timely release enough degradation products (polymeric debris) can activate macrophages to produce the required growth factors [acrd]*and*, in that way, can accelerate wound healing (Pratt, et al. (1994, "Dimehtyltitanocene-Induced Surface Chemical Degradation of Synthetic Bioabsorbable Polyesters", J. Polym. Sci. Part 0.4: Polym. Chem., 32(5):949; Greisler, (1988), "Small Diameter Vascular Prostheses: Macrophage-Biomaterial Interactions with Bioresorbable Vascular Prostheses". Transactions of ASAIO, 34:1051).

Mori, et al., U.S. Pat. No. 3,867, 520, discloses a delivery system for therapeutic agents using films made of polyamino acid polymers with oil-like or wax-like substances dispersed in the film. Therapeutic agents are dissolved in the carrier, and when the film is applied to an internal or external surface of the body, the carrier migrates to the surface of the film where the agent is released. However, these films are not biodegraded during use.

Sidman, U.S. Pat. No. 4,351,337, discloses an implantable delivery device comprising a matrix formed of a poly-alpha-amino acid component having one or more drugs and/or diagnostic agents physically contained therein. The drug or diagnostic agent is released through diffusion and/or biodegradation resulting from the action on the polymeric matrix of enzymes present in the host into which the implant is placed.

Taniharak, et al., U.S. Pat. No. 5,770,229, discloses a medical polymer gel made up of a cross-linked polysaccharide with a drug [attacked] *attached* to the polysaccharide via a linkage that is cleavable by an endogenous enzyme. This system provides for delayed release of the attached drug from the polymer, but the release rate is subject to individual variation in the amount of the endogenous enzyme, and the polymer, while biocompatible, is not biodegradable.

Kuroyangi and coworkers (1992, J. Appl. Biomater., 3:153-161) have developed a wound dressing for burn care that is a hydrophobic poly-L-leucine spongy matrix impregnated with antibacterial silver sulfadiazine supported by a fine nylon mesh. This wound dressing suppresses bacterial growth while controlling fluid loss. However, the dressing is not degraded, but rather sticks to the wound until it separates spontaneously from the healed skin.

Georgian Patent No. 1090 describes a wound dressing containing 45-50 wt. % biodegradable poly(ester-amide) based on natural alpha-amino acids impregnated with 50-55 wt. % dried bacteriophage. The poly(ester-amide) is not characterized in detail, but the dressing also has 0.05-0.15 wt. % surface immobilized alpha-chymotrypsin. The impregnated poly(ester-amide) is formed into a film, and the film is used to accelerate healing of superficial wounds, including burns.

Tsitlanadze, et al., in an abstract from Int. Symp. Biodegrad. Mater, Oct. 7-9, 1996, Hamburg, Germany, describe alpha-chymotrypsin-catalyzed hydrolysis of regular poly (ester-amides) (PEAs) of general formula I:

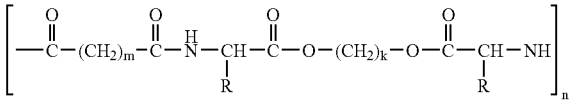

where k=2, 3, 4, or 6 m=4 or 8, and

R=$CH(CH_3)_2$, $CH_2CH(CH_3)_2$, $CH(CH_3)CH_2CH_3$, $(CH_2)_3CH_3$, $CH_2C_6H_5$, or $(CH_2)_3SCH_3$.

It is reported that alpha-chymotrypsin is spontaneously immobilized on the surface of the PEAs from aqueous solution, and erodes the polymer surface under physiologic conditions, with increasing lysis for more hydrophobic R groups and more hydrophobic polymer backbone. A biocomposite material based on a PEA polymer containing bacteriophages, antibiotic or anesthetic was prepared for study as artificial skin for healing burns and festering wounds.

SUMMARY OF THE INVENTION

The present invention provides bioerodable constructs for controlled release of bioactive materials. In a preferred mode, the constructs may be utilized adjacent to a biological surface. The constructs are based on a blend of two or more poly(ester-amide) polymers (PEA). Such polymers may be prepared by polymerization of diol (D), a dicarboxylic acid (C) and an alpha-amino acid (A) through ester and amide links in the form $(DACA)_n$. An example of a $(DACA)_n$ polymer is shown below in formula II. Suitable amino acids include any natural or synthetic alpha-amino acid, preferably neutral amino acids.

Diols may be any aliphatic diol, including alkylene diols like HO—$(CH_2)_k$—OH (i.e. non-branched), branched diols (e.g., propylene glycol), cyclic diols (e.g. dianhydrohexitols and cyclohexanediol), or oligomeric diols based on ethylene glycol (e.g., diethylene glycol, triethylene glycol, tetraethylene glycol, or poly(ethylene glycol)s). Aromatic diols (e.g. bis-phenols) are less useful for these purposes since they are more toxic, and polymers based on them have rigid chains that are less likely to biodegrade.

Dicarboxylic acids may be any aliphatic dicarboxylic acid, such as α,ω-dicarboxylic acids (i.e., non-branched), branched dicarboxylic acids, cyclic dicarboxylic acids (e.g. cyclohexanedicarboxylic acid). Aromatic diacids (like phthalic acids, etc.) are less useful for these purposes since they are more toxic, and polymers based on them have rigid chain structure, exhibit poorer film-forming properties and have much lower tendency to biodegrade.

Preferred PEA polymers have the formula II:

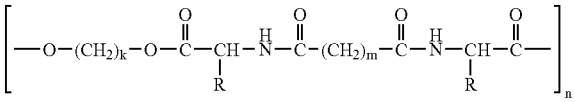

where k=2-12, especially 2, 3, 4, or 6, m=2-12, especially 4 or 8, and

R=$CH(CH_3)_2$, $CH_2CH(CH_3)_2$, $CH(CH_3)CH_2CH_3$, $(CH_2)_3CH_3$, $CH_2C_6H_5$, or [$(CH_2)_3SCH_3$]$(CH_2)_2SCH_3$.

The constructs optionally contain bioactive inclusions, which are released upon degradation (bioerosion) of the construct.

In a preferred embodiment, this invention provides biodegradable constructs which comprise a first PEA polymer in which A is L-phenylalanine (Phe-PEA) and a second PEA polymer in which A is L-leucine (Leu-PEA). Preferably, the ratio of Phe-PEA to Leu-PEA is from 10:1 to 1:1; more preferably, the ratio of Phe-PEA to Leu-PEA is from 5:1 to 2.5:1. The construct may be formed as a deformable sheet adapted to conform to a biological surface.

In another embodiment, this invention provides bioerodable constructs comprising PEA polymers and further comprising a bioactive agent, which may be selected from the group consisting of antiseptics, anti-infectives, such as bacteriophages, antibiotics, antibacterials, antiprotozoal agents, and antiviral agents, analgesics, anti-inflammatory agents including steroids and non-steroidal anti-inflammatory agents including COX-2 inhibitors, anti-neoplastic agents, contraceptives, CNS active drugs, hormones, and vaccines.

In yet another embodiment, the bioerodable construct of this invention comprises an enzyme capable of hydrolytically cleaving the PEA polymer, such as α-chymotrypsin. In a preferred embodiment, the enzyme is adsorbed on the surface of the construct. In a particularly preferred embodiment, the construct contains bacteriophage which are released by action of the enzyme.

This invention also provides a method of treating a patient having an ulcerative wound comprising inserting into the wound or covering the wound with a bioerodable construct according to claim 1, wherein the bioerodable construct contains a bioactive agent, which may be bacteriophage, an antibiotic, an antiseptic, or an analgesic. The wound treated by this invention may be open or infected, and the construct may be in the form of a deformable sheet. In a preferred embodiment, the construct used in treatment of the wound contains bacteriophage specific for bacteria found in the wound. The construct may also comprise an enzyme capable of hydrolytically cleaving the PEA polymer.

There is no currently available biodegradable polymer or polymeric blend composed entirely of naturally occurring and nontoxic building blocks showing high plasticity (e.g., pliability when hydrated) together with high enzyme-catalyzed biodegradation rates, solubility in common organic solvents like chloroform, and suitable for either impregnation or the spontaneous surface immobilization (adsorption) of the enzymes like trypsin, a-chymotrypsin, and lipase. The polymeric blends of this invention provide all of these properties, permitting their use as matrices for wound dressing/healing devices which are plastic and act to release bioactive substances in a sustained/controlled fashion.

BRIEF DESCRIPTION OF THE FIGURE

The FIGURE shows lipase catalyzed biodegradation of polymers in vivo over a six month period.

DETAILED DESCRIPTION OF THE EMBODIMENTS

Figure 1:
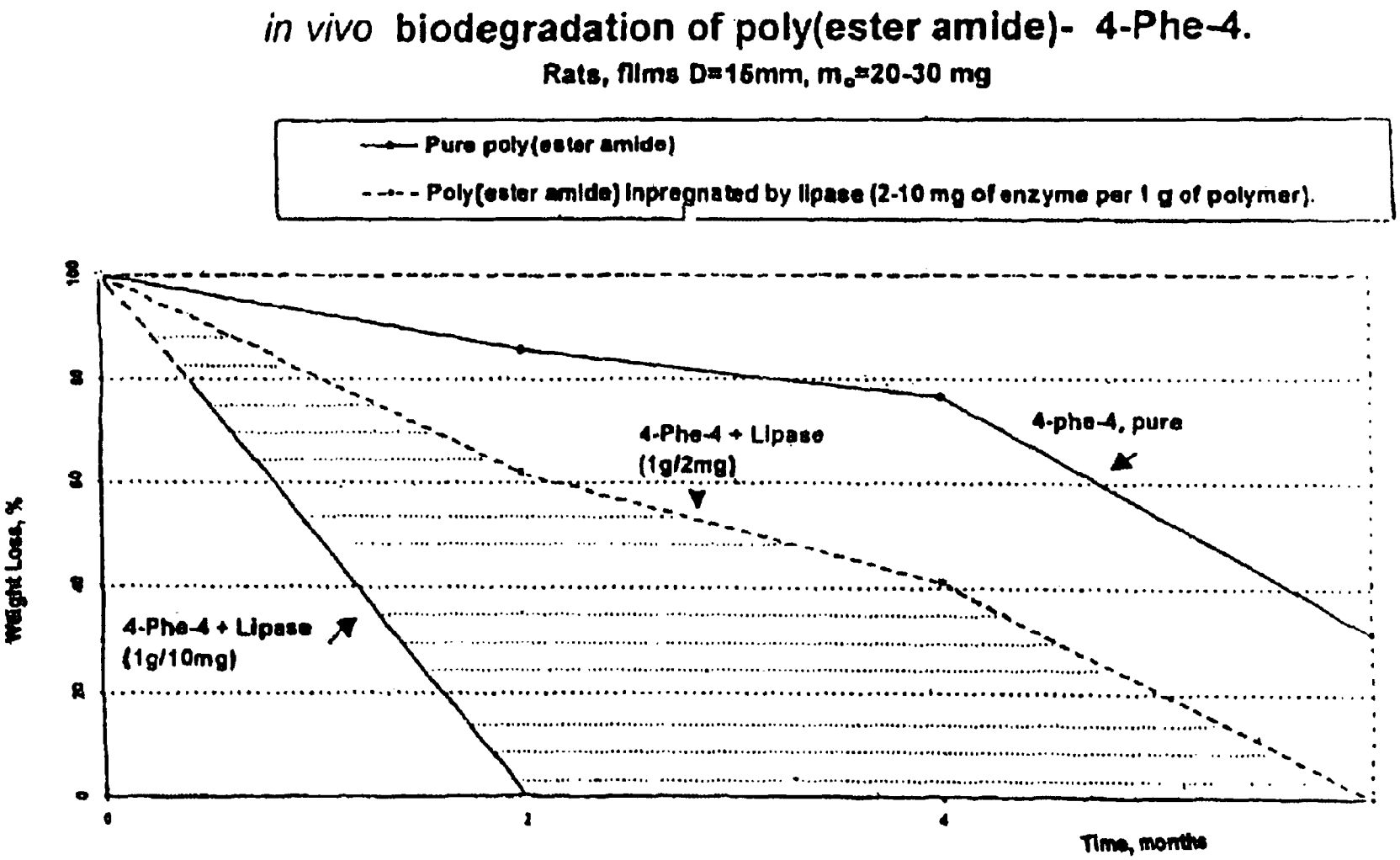

The use of a bacteriophage lysate in the treatment of suppurative lesions that are inflamed or infected requires multiple and frequent applications (e.g., 3-5 times a day) which increases consumption of both the bacteriophage preparation and the wound dressings. From this point of view the application of a bacteriophage reservoir, which provides for controlled release and prolonged action, is superior.

Bioresorbable (or bioerodable) polymers are the most appropriate matrices for preparing reservoirs of bacteriophages and/or other bioactive compounds. Bioactive composites based on bioerodable polymers are known for controlled release of drugs to provide desirable concentrations of bioactive substances in surrounding tissues. [Compositites] *Composites* made of bioerodable polymers disappear over time in a biological environment as the substance of the composite is [egraded] *degraded* or dissolved by action of the surrounding biologic milieu. This degradation may be facilitated by enzymes which catalyze cleavage of covalent bonds in the polymer. (Such enzymes may be present in the [bilologic mileu] *biologic milieu* or may be added exogenously, whether as part of the construct or otherwise.) Controlled or sustained release of a biologically active substance from a bioerodable construct refers to a delay in the dispersion of the biologically active substance relative to simple diffusion from its point of introduction into the biological environment. Controlled release is generally due to some factor which interferes with normal diffusion of the substance, such as a diffusion barrier or limited solubility of the diffusion substance. The bioerodable constructs of this invention present a diffusion barrier which is removed progressively as the polymer degrades.

More recently, it has also been established that the rapid release of polymer degradation products in a sufficient amount into the surrounding tissues activates macrophages for the production of growth factors, which may accelerate wound healing. It is beneficial for polymeric degradation products to be either normal metabolic components or easily digestible by cells. Polymers used as matrices should be plastic enough to tightly cover wounds. It is also highly desirable for the polymeric matrix to be able either to immobilize enzymes (e.g. trypsin, alpha-chymotrypsin, lipase, etc.) on the surface by a simple method or incorporate them in the bulk matrix. These enzymes can participate in the wound healing processes and can also erode polymers (e.g., by catalyzing the hydrolysis of ester bonds in the polymeric backbone) with a constant and desirable rate to provided for the release of bactericidal compounds as well as sufficient matrix degradation products in the surrounding tissue to stimulate macrophages.

The inventor has synthesized new biodegradable poly (ester-amide)s (PEAs) composed of naturally occurring alpha-amino acids, including essential ones like L-phenylalanine and L-leucine, and nontoxic compounds like aliphatic and dicarboxylic acids. Suitable synthetic methods are reported in Arabuli, et al. (1994), "Heterochain Polymers based on Natural Amino Acids. Synthesis and enzymatic hydrolysis of regular poly(ester-amide)s based on bis-(L-phenylalanine) alpha,omega-alkylene diesters and adipic acid," Macromol. Chem. Phys., 195(6):2279, and Katsarava, et al. (1998) "Amino Acid Based Bioanalogous Polymers. Synthesis and study of regular poly(ester-amide)s based on bis-(α-amino acid) α,ω-alkylene diesters and aliphatic dicarboxylic acid", J. Polym. Sci.: Part A: Chemistry, 37:391-407, the entirety of which are incorporated herein by reference. These rapidly bioresorbable, biocompatible poly (ester-amide)s may be used to form a bioerodable polymer matrix.

The poly(ester-amides) of this invention do not contain any toxic components. Alpha-amino acids, such as the essential amino acids L-phenylalanine and L-leucine, are naturally-occurring products. These normal metabolic components, upon release through biodegradation, are digested by cells. Fatty acids and diols are well known nontoxic products commonly used in the food industry. They are also used as building blocks for other classes of biodegradable polymers like poly anhydrides and poly-(ortho-ester)s approved by the U.S. Food and Drug Administration (FDA) for clinical trials and other practical applications.

It is very important that the poly(ester-amide)s used in this invention are soluble in organic solvents that do into inactivate bioactive compounds such as bacteriophages. These polymers are soluble in chloroform in which the enzymes like trypsin, α-chymotrypsin, lipase are sufficiently stable for enzyme activity to survive the process of preparing enzyme-containing polymer constructs.

Enzymes can be added to polymeric solutions in chloroform in order to form enzyme-containing polymeric matrices when the solution is cast onto glass plates and the solvent is evaporated. For polymeric films impregnated by enzymes according to this method, the enzymes catalyze the hydrolysis (erosion) of PEAs, which is important for the release of bioactive substances into the surrounding tissues. The biodegradation rates of PEAs can vary over a wide range, spanning, e.g., $10^1$-$10^3$ mg/$cm_2$ h. The degradation rate is a function of the enzyme activity in the composite. These polymers may be designed to release sufficient matrix degradation products (polymeric debris) over time to activate macrophages.

Enzymes may be spontaneously immobilized onto the surface of PEAs based on L-phenylalanine through the simple immersion of the polymeric films in aqueous enzyme solution for varying lengths of time. (Immersion for, e.g., for 15-20 min is typical.) PEAs based on L-leucine do not readily absorb enzymes using this simple method, and thus, PEAs based on L-phenylalanine are more suitable for preparing biodegradable matrices with surface-immobilized enzymes. However, PEAs based on L-phenylalanine do not possess sufficient plasticity for use as wound coverings. PEAs composed of L-leucine are pliable when hydrated (i.e., water acts as a plasticizer) and more suitable for biological applications such as wound coverings (dressings); however the films prepared from L-leucine PEAs are very sticky, adhering to themselves, and inconvenient to work with. In addition, L-leucine based PEAs immobilize enzymes poorly.

The present invention has discovered that the detrimental characteristics inherent in each class of PEAs can be overcome by blending them. Polymeric blends prepared from approximately 70% of L-phenylalanine based PEAs and 30% of L-leucine based PEAs showed:

good plasticity (necessary to cover wounds tightly), lack of self-adhesion, and ability to immobilize enzymes.

As contemplated by the present invention, the polymer blend which is the basis for the invention has sufficient plasticity to permit a film made with the polymer blend to be manually deformed to fit tightly to an irregular biological surface (e.g., a concave wound surface). Additionally, films made with the polymer blend are readily separable by gentle manual force, leaving each sheet of film intact upon separation. Finally, the surface of an object made with the polymer blend of this invention will absorb proteins, such that measurable enzyme activity can be detected adhered to the surface of the object after it is dipped into a solution of the enzyme.

This invention provides polymer blends comprising at least two PEAs of formula II. Preferably the blend contains one PEA in which R corresponds to the side chain of phenylalanine (Phe-PEA) and one PEA in which R corresponds to the side chain of leucine (Leu-PEA). The ratio of Phe-PEA to Leu-PEA may vary from 10:1 to 1:1, but is preferably from 5:1 to 2.5:1. Other PEAs (and indeed other polymers) may be included in the blend, so long as the resultant blend still exhibits the desired properties described above. The other polymers in the blend will, of course, be soluble in the solvent in which the blend is dispersed for preparing the constructs according to this invention. Leu-PEA and Phe-PEA are soluble in polar organic solvents including dimethyl-formamide (DMF), dimethylacetamide, dimethylsulfoxide (DMSO), trifluoroethanol, hexafluoroisopropanol and the like, or neutral organic solvents including chloroform and the like. Chloroform and similar solvents are preferred for preparation of bioerodable films containing bioactive components due to greater volatility (important for preparing films) and reduced tendency to inactivate enzymes (such as chymotrypsin or lipase), bacteriophages or other bioactive components.

In a preferred mode, the polymer blend of this invention is formed into a bioerodable film. The films of this invention may be a single layer or multiple layers, such as a bilayer film having one layer of a PEA blend and an adjacent layer of poly(siloxane elastomer). However, alternative bioerodable constructs using the polymer blend are easily within the skill of the art and within the contemplation of this invention. For example, the polymer blend may be used to provide a bioerodable coating on a support material which may or may not be biodegradable, such as a fibrous or non-fibrous three-dimensional construct or a woven support. Suitable forms for the three-dimensional [constrcts] *constructs* of this invention are foams, which may be formed by conventional means. For example, Phe-PEA/Leu-PEA blends can be prepared as foams as follows: a suspension of bacteriophages and other bioactive [substanses] *substances* (about 1 g) in the solution of Phe-PEA/Leu-PEA blend (1 g) in chloroform (10 mL) can be cast onto hydrophobic surface and 90-99% of chloroform evaporated at r.t. under atmospheric pressure. Afterwards a reduced pressure may be applied at room temperature to remove residual chloroform, and the resulting foamed film dried for 12 h under reduced pressure. According to another procedure 1-10% (of chloroform volume) of n-pentane may be added to the suspension above. The mixture may be cast onto *a* hydrophobic surface and allowed to dry at room temperature for 24 h, and the foamed film may be subjected to a final drying under reduced pressure for 12 h. Foamed films may also be obtained using ultrasonic disintegration techniques.

Constructs prepared with the polymers of this invention may be part of devices including a support material to be used as, for example, bandages for wounds or burn dressings. Of course, the blends forming a coating on a woven support will preferably retain the flexibility and/or elasticity of blends used for film-forming, but a blend for coating a rigid, three-dimensional construct may be less elastic. Such blends may have higher Phe-PEA content, and coatings in which Phe-PEA is the only PEA polymer are within the contemplation of this invention for such applications.

In another mode, this invention contemplates constructs consisting all or in part of a blend according to this invention which may be surgically implanted. Constructs according to this invention may also be formed into devices for wound packing, such as gel foams, or may be used as components in surgical appliances, such as Penrose drains, indwelling catheters, catheters for peritoneal dialysis, and any other appliances that are in contact with body cavities, the blood circulation, or the lymphatic circulation and are either used to treat potential infections or are at risk of becoming infected. This invention also contemplates appliances for oral hygiene, including gum implants (e.g., for periodontal disease or dental caries). Such constructs will preferably contain bioactive material released in a controlled manner upon erosion of the construct. Suitable selections of particular bioactive inclusions will be readily apparent to the skilled artisan in view of the intended site of implantation. For example, composites containing bactericidal [agenst] *agents* such as bacteriophage may be implanted in the body to treat osteomyelitis, etc. Alternatively, bioerodable composites of this invention could be used for sustained/controlled release of anticancer and/or other drugs at a target site. Bioactive materials may be released in a controlled fashion by diffusion from within the construct, or by degradation of the construct, or by a combination of these processes.

Bioactive and/or inactive biocompatible materials may be included in the erodable construct in amounts up to 60% or more by weight, so long as their inclusion does not destroy the desirable properties of films according to this invention. Bioactive materials contemplated for inclusion in the bioerodable constructs of this invention include, but are not limited to, antiseptics, anti-infectives, such as bacteriophages, antibiotics, antibacterials, antiprotozoal agents, and antiviral agents, analgesics, anti-inflammatory agents including steroids and non-steroidal anti-inflammatory agents including COX-2 inhibitors, anti-neoplastic agents, contraceptives, CNS active drugs, hormones, and vaccines. In particular, constructs may include one or more of calcium gluconate and other phage stabilizing additives, hyaluronidase, fibrinolysine and other fibrinolytic enzymes, methyluracyl and other agents stimulating metabolic processes, sodium hydrocarbonate, L-arginine and other vasodilators, Benzocaine and other pain killers, mono- and disaccharides, polysaccharides and mucopolysaccharides, Metronidazol and other anti-protozoa drugs, Clotrimazolum and other anti-fungal drugs, thrombine and other hemostatics, vitamins, Prednizolone and other anti-inflammatory steroids, and Voltaren (Sodium diclofenac) and other anti-inflammatory non-steroid drugs. Of course the skilled artisan will in any case confirm that particular construct formulations retain the desired properties as discussed herein, and constructs which exhibit none of these properties are outside the contemplation of this invention.

In one preferred mode, this invention provides a novel approach to management of poorly healing and poorly vascularized wounds (which may include diabetic foot ulcers, pressure ulcers in patients with reduced mobility, and other ulcers and open skin [lesions]*lesions*). In medicine, poorly healing wounds, such as those seen in diabetic patients with foot ulcers, and in bedridden patients with pressure sores, represent a major and very expensive management problem. Use of antibiotics in this setting is generally not efficacious. Because of poor vascularization, antibiotics seldom achieve therapeutic levels in affected areas sufficient to eradicate infection. Moreover, because of the recurrent courses of antibiotics that such patients have often received, the bacterial pathogens causing the infections are often antibiotic resistant. In this mode, as well as other wound treatment embodiments, the controlled-release character of the polymer constructs according to this invention avoid the necessity of constant re-application of bactericidal material, as well as the need for associated dressing changes.

Biocomposites mediating a sustained/controlled release of appropriate therapeutic agents have proven to be especially efficacious for healing infected wounds and cavities. Film materials, so called "artificial skin", prepared from these biocomposites have important therapeutic effects:

Polymer material, when applied to the surface of such wounds, acts as a protector from external mechanical actions and bacterial invasion, and further prevents heat and moisture loss that occur as a result of uncontrolled water evaporation from the injured surface; and The slow-release properties of the biologically-active compound can be exploited to promote appropriate, steady release of anti-bacterial agents at the site of infection.

Use of biocomposite "artificial skin" does not require patient immobilization, and thereby facilitates a return to daily life activities, an important consideration in this class of patients.

A key element in the management of chronically infected wounds is the suppression of pathogenic bacterial flora. With biocomposite materials, this can be achieved by introducing bacteriocidal substances into the biocomposite structure. Antibiotics may be used in this setting, but their efficacy is increasingly limited by the development of antibiotic resistance. More recently, there has been interest in the introduction into biocomposites of such bactericidal substances as silver sulfadiazine (and related diazine derivatives of sulfanilamide), furagin (and pharmaceutically acceptable salts thereof) and chlorohexydine (and pharmaceutically acceptable salts thereof). However, utilization of such compounds may be limited by their inherent toxicity, particularly for patients with underlying kidney or liver disease.

Incorporation of bacteriophages into such biocomposite materials provides an alternative approach. Bacteriophage are viruses that kill specific bacteria. The lysis of microorganisms by viruses was discovered at the beginning of the 20th century. Any one phage tends to be highly specific for certain bacteria, requiring that therapy be carefully targeted (i.e., there is no analogy to the broad-spectrum antibiotics which can "kill everything"). However, this also means that phage therapy can be used to kill specific pathogens without disturbing normal bacterial flora.

Phages have been reported to be effective in treating skin infections caused by Pseudomonas, Staphylococcus, Klebsiella, Proteus, E. coli, and other pathogenic species; success rates in these studies have ranged from 75 to 100%, depending on the pathogen. However, for these studies bacteriophages were introduced in a variety of vehicles: aqueous liquid preparations, aerosols and creams.

The polymeric blend composed of L-phenylalanine, L-leucine, adipic acid, and butane-diol-1,4 has been successfully used for preparing bioactive composites containing bactericidal substances. The wound dressings obtained based on this biocomposite material showed high wound healing properties.

Starting from the materials mentioned above it seems that bioactive composite based on bioresorbable (bioerodable) polymer and containing a complex of bacteriophages as a bactericidal substance will be an effective dressing material with accelerated wound healing ability. Selection of suitable bacteriophage is described in U.S. Provisional Patent Application No. 60/175,415, entitled "Bacteriophage Specific for Vancomycin Resistant Enterococci (VRE)", filed Jan. 11, 2000, and U.S. Provisional Patent Application Nos. 60/175,416, filed Jan. 11, 2000, and 60/205,240, filed May 19, 2000, both entitled "Method And Device For Sanitation Using A Bacteriophage", the disclosures of which are incorporated by reference in their entireties.

EXAMPLE

A complex of polyvalent bacteriophages directed toward Staphylococcus species, Streptococcus species, E. coli, Proteus species, and Pseudomonas aeruginosa with a titer of $2\times10^6$-$2\times10^7$ plaque-forming units, was prepared and used as bioactive substance for this study. Bacteriophage were prepared as a lyophilized dry powder as follows: bacteriophages suspended in an aqueous sucrose-gelatin mixture were lyophilized, resulting in a dry mass that was ground into fine powder. In this process, 50 mg of dry preparation corresponds to 1 ml of liquid bacteriophage with a titer of $2\times10^6$-$2\times10^7$. None of the individual components of bioactive composites (polymer, organic solvent, alpha-chymotrypsin, lipase) affected bacteriophages activity—100% of starting activity was retained in all cases.

A bioactive film was prepared as follows: A fine suspension of dry bacteriophage in a polymer solution with an appropriate solvent was cast on a glass surface and dried to constant weight. A composite was obtained in the from of a film with the following characteristics: mass 1 g, film area—65-65 $cm^2$, thickness—0.2-0.3 mm. Afterwards alpha-chymotrypsin was immobilized on the surface of the film. Optionally, the film was perforated. For particular applications, analgesics and/or antibiotics were added to the composite as well.

The activity of the resultant film in in vitro experiments was determined using a bacterial lawn on solid media. Activity was estimated by measuring the width of the zone of lysis. The activity of the film coincides with the activity of dry bacteriophages used; pure polymeric film did not reveal any bactericidal activity.

The kinetics of bacteriophage release from 9 cm disks of the film was studied in phosphate buffer under physiological conditions (see Table 1). One can see that release of bacteriophages during first 24 hours both from α-chymotrypsin-immobilized and α-chymotrypsin-free films was comparable; for enzyme-immobilized film it was only 1.5-2 times higher. This can be explained by extensive desorption of bacteriophages from the surface zone of enzyme free film. However, when the films were transferred to fresh buffer at 24 hours and 120 hours, the enzyme-catalyzed erosion mechanism became important at later stages for releasing bacteriophages from the bulk of the film, and difference in release rate reached more than one order in magnitude. Clearly, alpha-chymotrypsin promotes the release of bacteriophages from bioactive composite.

TABLE

Sustained Release of Bacteriophages and Antibiotics from Medicated Wound Covering Film Release of bacteriophages from 9 cm dia. Phe-PEA film disks into 10 mL of Phosphate buffer 0.2 M, pH 7.4, T = 37° C. A 9 cm Phe-PEA/bacteriophage film disk contains approximately $1800\times10^4$ bacteriophages.

| | Titer of bacteriophages in 1 mL solution | |
|---|---|---|
| Time in hours | Composite bacteriophage/Phe-PEA film with α-chymotrypsin | Composite bacteriophage/Phe-PEA film without surface-immobilized α-chymotrypsin |
| 1 | $2.0\times10^4$ | $1.3\times10^4$ |
| 3 | $5.0\times10^4$ | $3.0\times10^4$ |
| 24 | $8.0\times10^4$ | $4.0\times10^4$ |
| 24 h later, after transfer to a new 10 mL portion of the buffer | | |
| 1 | $3.2\times10^4$ | $1.3\times10^4$ |
| 3 | $9.0\times10^4$ | $3.1\times10^4$ |
| 96 | $200.0\times10^4$ | $90.0\times10^4$ |
| 120 h later, after transfer to a new 10 mL portion of the buffer | | |
| Time in hours | Composite bacteriophage/Phe-PEA film with α-chymotrypsin | Composite bacteriophage/Phe-PEA film without surface-immobilized α-chymotrypsin |
| 1 | $2.5\times10^4$ | $0.06\times10^4$ |
| 4 | $5.0\times10^4$ | $0.20\times10^4$ |

It should be noted that surface immobilized α-chymotrypsin can play an additional role namely it can decompose both peptides and denaturated proteins. this enzymatic debridment, as it is known from literature, leads to the sanitation of a wound and accelerates healing.

The activity of films according to this invention was checked periodically for 1.5 years against both preexisting laboratory strains and newly received bacterial strains, and the film retained activity over this period. The surface immobilized enzyme was active for this period as well. The FIGURE shows lipase catalyzed biodegradation of polymers in vivo over a six month period. The in vivo data is summarized in Table 2.

TABLE 2

In vivo Degradation of Biocomposites

| Sample | Number of rats | Number of films per one rat | Duration (days) | Result |
|---|---|---|---|---|
| 4-L-Phe-4 | 2 | 2 | 109 | Films were completely absorbed, in one case a trace of connective tissue capsule was observed. |
| 4-L-Phe-4 | 2 | 2 | 123 | Films were completely absorbed, no trace of tissue reaction was observed |
| 4-L-Phe-4 | 2 | 2 | 175 | Films were completely absorbed, no trace of tissue reaction was observed. |

TABLE 2-continued

In vivo Degradation of Biocomposites

| Sample | Number of rats | Number of films per one rat | Duration (days) | Result |
|---|---|---|---|---|
| 4-L-Phe-4-Lip | 3 | 2 | 39 | In 2 rats films were completely absorbed, in one rat both films were [incapsulated*]*encapsulated**. |
| 4-L-Phe-4-Lip | 1 | 2 | 42 | Films were completely absorbed, no trace of tissue reaction was observed. |
| 4-L-Phe-4-Lip | 4 | 4 | 44 | Films were completely absorbed, no trace of tissue reaction was observed. |
| 4-L-Phe-4-Lip | 1 | 2 | 45 | Both films were [incapsulated*]*encapsulated**. |
| 4-L-Phe-4-Lip | 5 | 3 | 77 | 14 films were completely absorbed, only one film was [incapsulated*]*encapsulated**. |
| 4-L-Phe-4-Lip | 2 | 2 | 145 | Films were completely absorbed, no trace of tissue reaction was observed. |

*In these cases lipase was found to be inactivated, that is it did not catalyze the hydrolysis of poly(ester amide).
Totally 57 films (each 20-25 mg) were implanted subcutaneously [to]*into* rats, 52 films were completely absorbed. Only 5 films of 4-L-Phe-4-Lip series were [incapsulated]*encapsulated* owing to enzyme inactivation.
4-L-Phe-4-PEA based on L-phenylalanine, adipic acid, and butanediol-1,4,4-L-Phe-4-Lip - the same, lipase impregnated (10 mg lipase per 1 g of PEA).

What is claimed is:

1. A bioerodable construct for controlled release of bioactive materials, said construct comprising a blend of *at least* two poly(ester-amide) polymers (PEA) prepared by polymerizing a diol (D), *wherein the diol (D) is not bisphenol;* a dicarboxylic acid (C), *wherein the dicarboxylic acid (C) is not phthalic acid;* and an alpha-amino acid (A) through ester and amide links in the form $(DACA)_n$[.],

[wherein the PEA polymer has the formula:

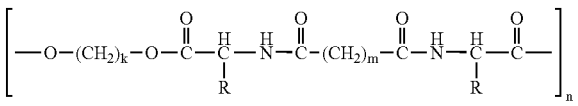

wherein k=2-12, m=2-12, and

R=$CH_2CH(CH_3)_2$, or $CH_2C_6H_5$.

and,]

wherein the *blend comprises a first PEA polymer in which A is phenylalanine (Phe-PEA) and a second PEA polymer in which A is leucine (Leu-PEA) at a* ratio of Phe-PEA to Leu-PEA [is from] *of* 10:1 to 1:1.

[2. The construct of claim 1, wherein k=2, 3, 4, and 6 and m=4 or 8.]

3. The construct of claim 1, wherein the ratio of Phe-PEA to Leu-PEA is 5:1 to 2.5:1.

4. The construct according to any one of claims 1[,2] or 3, wherein the construct is a deformable sheet adapted to conform to a biological surface.

5. The construct according to claim 4, further comprising a bioactive agent.

6. The construct of claim 5, wherein the bioactive agent is selected from the group consisting of antiseptics, anti-infectives, such as bacteriophages, antibiotics, antibacterials, antiprotozoal agents, and antiviral agents, analgesics, anti-inflammatory agents [including] *selected from the group consisting of* steroids and non-steroidal anti-inflammatory agents [including] *selected from the group consisting of* COX-2 inhibitors, anti-neoplastic agents, contraceptives, CNS active drugs, hormones, and vaccines.

7. The construct according to claim 5, wherein the construct comprises an enzyme capable *of* hydrolytically cleaving the PEA polymer.

8. The construct according to claim 7, wherein the enzyme is α-chymotrypsin.

9. The construct according to claim 7, wherein the enzyme is adsorbed on the surface of the construct.

10. The construct according to claim 7, wherein the construct contains *a* bacteriophage which [are] *is* released by action of the enzyme.

11. A method of treating a patient having an ulcerative wound comprising inserting into the wound or covering the wound with a bioerodable construct according to claim 1, wherein the bioerodable construct is a deformable sheet containing a bioactive agent.

12. The method of claim 11, wherein the bioactive agent [is] *comprises a* bacteriophage, an antibiotic, an antiseptic, or an analgesic.

13. The method of claim 11, wherein the wound is open or infected.

14. The method according to claim 12, wherein the bacteriophage are specific for bacteria found in the wound.

15. The method according to any one of [claim] *claims* 11-14, wherein the construct also comprises an enzyme capable of hydrolytically clearing the PEA polymer.

16. The construct according to any one of claims 1[, 2] or 3, further comprising a bioactive agent.

17. The construct of claim 16, wherein the bioactive agent is selected from the group consisting of antiseptics, anti-infectives, [such as] bacteriophages, antibiotics, antibacterials, antiprotozoal agents, and antiviral agents, analgesics, anti-inflammatory agents [including] *selected from the group consisting of* steroids and non-steroidal anti-inflammatory agents [including] *selected from the group consisting of* COX-2 inhibitors, anti-neoplastic agents, contraceptives, CNS active drugs, hormones, and vaccines.

18. The construct according to any one of claims 1[, 2] or 3, wherein the construct comprises an enzyme capable of hydrolytically cleaving the PEA polymer.

19. The construct according to claim 18, wherein the enzyme is α-chymotrypsin.

20. The construct according to claim 18, wherein the enzyme is adsorbed on the surface of the construct.

21. The construct according to claim 18, wherein the construct contains *a* bacteriophage which [are] *is* released by action of the enzyme.

*22. The construct according to claim 1 wherein the blend is formed into a bioerodable coating on a support material or is formed into a bioerodable film.*

23. The construct according to claim 22 wherein the blend is formed into a bioerodable coating comprising bioactive material.

24. The construct according to claim 1 wherein the construct is a device that can be surgically implanted.

25. The construct according to claim 24 wherein the implantable device is an indwelling catheter or appliance for oral hygiene.

26. A bioerodable construct for controlled release of bioactive materials, said construct comprising a blend of at least two poly(ester-amide) polymers (PEA), wherein each PEA polymer has the formula:

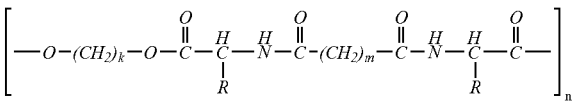

wherein k=2-12, m=2-12, and $R=CH(CH_3)_2$, $CH_2CH(CH_3)_2$, $CH(CH_3)CH_2CH_3$, $(CH_2)_3CH_3$, $CH_2C_6H_5$, or $(CH_2)_2SCH_3$, wherein the blend comprises a PEA polymer wherein $R=CH_2CH(CH_3)_2$ or a PEA polymer wherein $R=CH_2C_6H_5$.

27. The construct according to claim 26, wherein the blend comprises a first PEA polymer wherein $R=CH_2CH(CH_3)_2$, and a second PEA polymer wherein $R=CH_2C_6H_5$.

28. The construct of claim 27, wherein the first PEA polymer and second PEA polymer are present in a ratio of 10:1 to 1:1.

29. The construct of claim 28, wherein the ratio of first PEA polymer to second PEA polymer is 5:1 to 2.5:1.

30. The construct of claim 26, wherein k=2, 3, 4, or 6 and m=4 or 8.

31. The construct according to claim 26, wherein the construct is deformable sheet adapted to conform to a biological surface.

32. The construct according to claim 31, further comprising a bioactive agent.

33. The construct of claim 32, wherein the bioactive agent is selected from the group consisting of antiseptics, anti-infectives, bacteriophages, antibiotics, antibacterials, anti-protozoal agents, and antiviral agents, analgesics, anti-inflammatory agents selected from the group consisting of steroids and non-steroidal anti-inflammatory agents selected from the group consisting of COX-2 inhibitors, anti-neoplastic agents, contraceptives, CNS active drugs, hormones, and vaccines.

34. The construct according to claim 32, wherein the construct comprises an enzyme capable of hydrolytically cleaving the PEA polymer.

35. The construct according to claim 34, wherein the enzyme is α-chymotrypsin.

36. The construct according to claim 34, wherein the enzyme is adsorbed on the surface of the construct.

37. The construct according to claim 34, wherein the construct contains a bacteriophage which is released by action of the enzyme.

38. A method of treating a patient having an ulcerative wound comprising inserting into the wound or covering the wound with a bioerodable construct according to claim 26, wherein the bioerodable construct is a deformable sheet containing a bioactive agent.

39. The method of claim 38, wherein the bioactive agent comprises a bacteriophage, an antibiotic, an antiseptic, or an analgesic.

40. The method of claim 38, wherein the wound is open or infected.

41. The method according to claim 39, wherein the bacteriophage is specific for bacteria found in the wound.

42. The method of claim 38, wherein the construct also comprises an enzyme capable of hydrolytically cleaving the PEA polymer.

43. The construct according to claim 26 further comprising a bioactive agent.

44. The construct of claim 43, wherein the bioactive agent is selected from the group consisting of antiseptics, anti-infectives, bacteriophages, antibiotics, antibacterials, anti-protozoal agents, and antiviral agents, analgesics, anti-inflammatory agents selected from the group consisting of steroids and non-steroidal anti-inflammatory agents selected from the group consisting of COX-2 inhibitors, anti-neoplastic agents, contraceptives, CNS active drugs, hormones, and vaccines.

45. The construct according to claim 26, wherein the construct comprises an enzyme capable of hydrolytically cleaving the PEA polymer.

46. The construct according to claim 45, wherein the enzyme is α-chymotrypsin.

47. The construct according to claim 45, wherein the enzyme is adsorbed on the surface of the construct.

48. The construct according to claim 45, wherein the construct contains a bacteriophage which is released by action of the enzyme.

49. The construct according to claim 26 wherein the blend is formed into a bioerodable coating on a support material or is formed into a bioerodable film.

50. The construct according to claim 49 wherein the blend is formed into a bioerodable coating comprising bioactive material.

51. The construct according to claim 26 wherein the construct is a device that can be surgically implanted.

52. The construct according to claim 51 wherein the implantable device is an indwelling catheter or appliance for oral hygiene.

53. A bioerodable construct for controlled release of bioactive materials, said construct comprising a blend of at least two poly(ester-amide) polymers (PEA) prepared by polymerizing a diol (D), wherein the diol (D) is not bisphenol; a dicarboxylic acid (C), wherein the dicarboxylic acid (C) is not phthalic acid; and an alpha-amino acid (A) through ester and amide links in the form $(DACA)_n$, wherein the alpha-amino acid (A) of each PEA polymer of the blend is selected from the group of amino acids having aliphatic side chains, amino acids having sulfur-containing side chains, and amino acids having side chains containing aromatic rings, and wherein the alpha-amino acid of at least one of the PEA polymers is phenylalanine or leucine.

54. The construct of claim 53 wherein the amino acid having aliphatic side chains is selected from valine, leucine, isoleucine, and norleucine.

55. The construct of claim 53, wherein the amino acid having sulfur-containing side chains is methionine.

56. The construct of claim 53, wherein the amino acid having side chains containing aromatic rings is phenylalanine.

57. The construct of claim 53 the blend comprises a first PEA polymer in which A is phenylalanine and a second PEA polymer in which A is leucine.

58. A bioerodable construct for controlled release of bioactive materials, said construct comprising a blend of at least two poly(ester-amide) polymers (PEA), wherein each PEA polymer has the formula:

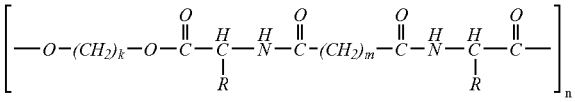

*wherein*

*k=2-12,*

*m=2-12,*

*wherein R represents an amino acid side chain, and the amino acid side chain is selected from aliphatic side chains, sulfur-containing side chains, and side chains containing aromatic rings, and*

*wherein the blend comprises a PEA polymer wherein R is an amino acid side chain containing an aromatic ring or a PEA polymer wherein R is an aliphatic amino acid side chain.*

*59. The construct of claim 58 wherein the aliphatic amino acid side chain is selected from valine, leucine, isoleucine, and norleucine side chains.*

*60. The construct of claim 58, wherein the sulfur-containing side chain is a methionine side chain.*

*61. The construct of claim 58, wherein the side chain containing aromatic rings is a phenylalanine side chain.*

*62. The construct of claim 58 the blend comprises a first PEA polymer in which R is a phenylalanine side chain, and a second PEA polymer in which R is a leucine side chain.*

*63. The construct according to claim 1 wherein the construct is a device for wound packing.*

*64. The construct according to claim 63 wherein the construct is a foam.*

*65. The construct according to claim 53 wherein the construct is a device for wound packing.*

*66. The construct according to claim 65 wherein the construct is a foam.*

* * * * *